US00PP19024P3

(12) United States Plant Patent
Cain et al.

(10) Patent No.: US PP19,024 P3
(45) Date of Patent: Jul. 15, 2008

(54) GRAPEVINE PLANT NAMED 'SUGRATHIRTYTWO'

(50) Latin Name: *Vitis vinifera*
Varietal Denomination: Sugrathirtytwo

(75) Inventors: David W. Cain, Bakersfield, CA (US); Michael J. Striem, Bakersfield, CA (US)

(73) Assignee: Sun World International, LLC, Bakersfield, CA (US)

( * ) Notice: Subject to any disclaimer, the term of this patent is extended or adjusted under 35 U.S.C. 154(b) by 319 days.

(21) Appl. No.: 11/329,258

(22) Filed: Jan. 10, 2006

(65) Prior Publication Data

US 2007/0163018 P1 Jul. 12, 2007

(51) Int. Cl.
*A01H 5/00* (2006.01)

(52) U.S. Cl. ..... Plt./205

(58) Field of Classification Search ..... Plt./205
See application file for complete search history.

(56) References Cited

U.S. PATENT DOCUMENTS

PP10,434 P 6/1998 Cain

*Primary Examiner*—Anne Marie Grunberg
*Assistant Examiner*—Georgia Helmer
(74) *Attorney, Agent, or Firm*—Knobbe Martens Olson & Bear LLP

(57) ABSTRACT

A new and distinct grapevine variety characterized by producing red skinned, aromatic flavored, elliptical berries that have an excellent eating quality. The berries ripen early to mid-season, having a naturally medium size, a crisp flesh texture, and have medium and up sugar content.

1 Drawing Sheet

Latin name of the genus and species claimed: *Vitis vinifera.*
Variety denomination: 'Sugrathirtytwo'.

BACKGROUND AND SUMMARY OF THE INVENTION

This invention relates to the discovery and asexual propagation of a new variety of grapevine as herein described and illustrated. The new variety was first hybridized by David W. Cain and Michael J. Striem in Wasco, Kern County, Calif., the variety being originated by controlled hybridization and subsequent culture of seed traces and embryo rescue procedures. The new variety 'Sugrathirtytwo' is characterized by producing early-mid-season ripening, aromatic flavored, red skinned, seedless grapes. The berries have a naturally medium size, and an elliptic shape, crisp flesh texture, medium and up sugar content and excellent eating quality. 'Sugrathirtytwo' is exceptional with its read color development when ripening even under hot weather. The new variety 'Sugrathirtytwo' ripens at about the same time as 'Sugrathirteen' (U.S. Plant Pat. No. PP10,434), and about seven days after 'Flame Seedless' (unpatented), as grown in the Wasco area, California.

The seed parent is the varietal selection '88124-037-243' (unpatented) and the pollen parent is the varietal selection '88047-004-226' (unpatented). The parent varieties were first crossed in May, 1994, by David W. Cain and Michael J. Striem. The new variety was created by hybridization of two "seedless" grapes possessing small, abortive, vestigial ovules. From the initial population of hybrid ovules, embryo rescue methods were used to produce a population from which the present variety was selected. The date of first sowing was August, 1994, and the date of first flowering was May, 1996.

The new variety 'Sugrathirtytwo' was first propagated in December, 1998, in Wasco, Kern County, Calif., by Dr. David Cain using hardwood cuttings.

The new variety 'Sugrathirtytwo' resembles its seed parent '88124-037-243' in many characteristics, such as berry color, but differs from its seed parent in having much larger berries (3.88 gr) as compared to the berries of the seed parent (2.73 gr). Additionally, 'Sugrathirtytwo' ripens approximately 1–2 weeks after the seed parent.

The new variety 'Sugrathirtytwo' differs from its pollen parent '88047-004-226' in that the berries of the pollen parent are creamy-white and much smaller (1.97 gr) than those of the new variety 'Sugrathirtytwo' (3.88 gr). Additionally, 'Sugrathirtytwo' ripens approximately 1–2 weeks after the pollen parent.

The new variety 'Sugrathirtytwo' resembles the comparable variety 'Flame Seedless' in its color and ripening window. However, the berries of 'Sugrathirtytwo' are more oval, not as crunchy and not as round as the berries of 'Flame Seedless.' The berries of the new variety 'Sugrathirtytwo' develop full uniform red color, and do not crack as easy as those of 'Flame Seedless.' The eating quality of the new variety 'Sugrathirtytwo' differs from 'Flame Seedless' in that the berries of 'Sugrathirtytwo' have anew aromatic flavor, compared with the neutral flavor of the 'Flame Seedless' berries.

The new 'Sugrathirtytwo' variety has been shown to maintain its distinguishing characteristics through successive asexual propagations by, for example, cuttings.

Variations of the usual magnitude from the described above many occur with changes in growing conditions, irrigation, fertilization, pruning, management and climatic variations.

BRIEF DESCRIPTION OF THE FIGURE

The accompanying drawing in FIG. 1 illustrates in full color a typical cluster of berries, a young shoot, and a mature leaf blade of the new grapevine at 5 years of age. The colors are as nearly true as is reasonably possible in a color representation of this type.

DETAILED BOTANICAL DESCRIPTION OF THE INVENTION

Figure 1:
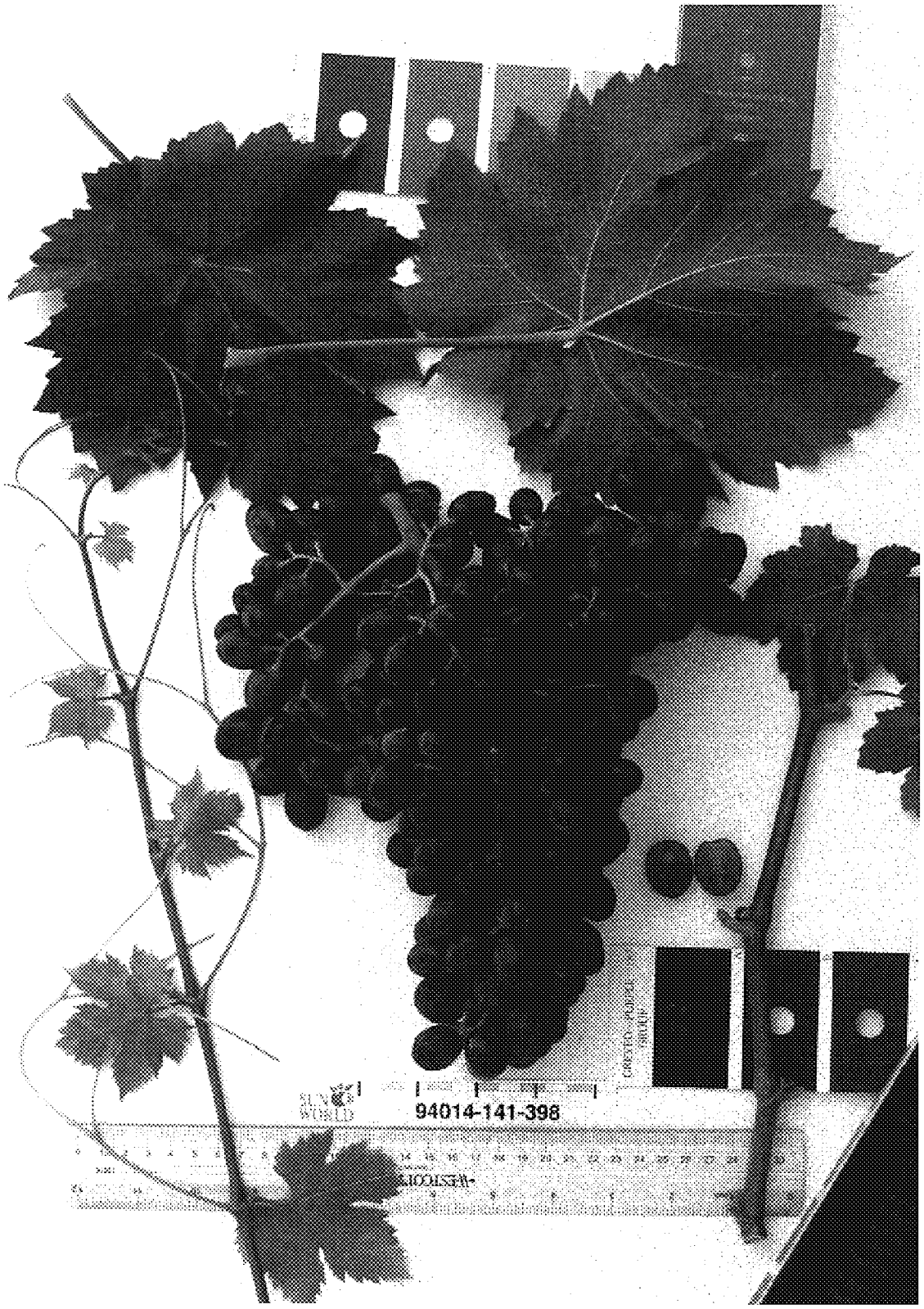

Throughout this specification, color names beginning with a small letter signify that the name of that color, as used in common speech, is aptly descriptive. Color names beginning with a capital letter designate values based upon the R.H.S. Colour Chart, published by The Royal Horticultural Society, London, England.

Many of the description values in this specification are based on and conform to those set forth by the International Board for Plant Genetic Resources Institute Grape Descriptors (Vitis spp.) of 1983 and/or 1997 which was developed in collaboration with the Office International de la Vigne et du Vin (OIV) and the International Union for the Protection of New Varieties of Plants (UPOV).

The descriptive matter which follows pertains to 'Sugrathirtytwo' plants grown in the vicinity of Wasco, Kern County, Calif. during 2002, 2003, and 2004, and is believed to apply to plants of the variety grown under similar conditions of soil and climate elsewhere:

VINE

General:

*Planting.*—Trained on 'Cross-Arm'/T trellis, planted in a 7 ft.×12 ft. spacing.

*Practices.*—Gene-pool-vine: Cane pruned to approximately 6 canes per vine and trimmed once in the early summer. Test-vines: Spur pruned to approximately 12 to approximately 18 two-bud-spurs per vine, and tested also as cane pruned to approximately 6 canes per vine.

*Size.*—Medium. Height: Approximately 1.80 to 2.15 m. Width: Approximately 1.75 to 1.95 m.

*Vigor.*—Vigorous.

*Fresh pruning weight.*—Approximately 11.88 kg per vine.

*Density of foliage.*—Medium.

*Productivity.*—Medium productive — approximately 77 clusters per vine.

*Yield.*—Approximately 17.96 kg per vine, thinned to approximately 24 cluster per vine.

*Crop load.*—Approximately 1.52 kg per vine (kg fruit per kg fresh-pruning-weight).

*Root stock.*—Not applicable.

*Own root.*—Yes.

Trunk:

*Shape.*—Slender.

*Diameter.*—Approximately 66 mm.

*Straps.*—Very long.

*Surface texture.*—Smooth.

*Inner bark color.*—Near Greyed-orange 177B.

*Outer bark color.*—Near Brown 200D with near Grey 201A.

SHOOTS

Young shoot:

*Form. of tip.*—Wide open.

*Distribution of anthocyanin coloration of tip.*—Absent.

*Intensity of anthocyanin coloration of tip.*—Absent.

*Density of prostrate hairs on tip.*—Very sparse.

*Density of erect hairs on tip.*—Absent.

Woody shoot (Mature canes):

*Shape.*—Slender.

*Internode length.*—Approximately 52 mm.

*Width at node.*—Approximately 12 mm.

*Cross section.*—Circular.

*Surface.*—Smooth.

*Main color.*—Near Greyed-orange 166C.

*Lenticels.*—Absent.

*Density of erect hairs on nodes.*—None or very sparse.

*Density of erect hairs on internodes.*—None or very sparse.

*Growth of axillary shoots.*—Strong, approximately 14 cm.

Flowering shoot:

*Attitude during flowering on shoots which are not tied.*—Erect.

*Color of dorsal side of internodes.*—Near Yellow-green 144A.

*Color of ventral side of internodes.*—Near Yellow-green 144B with near Greyed-purple 183A stripes.

*Color of dorsal side of nodes.*—Near Yellow-green 144A.

*Color of ventral side of nodes.*—Near Yellow-green 144A.

*Density of erect hairs on nodes.*—None.

*Erect hairs on internode.*—Absent.

*Density of prostrate hairs on nodes.*—None.

*Density of prostrate hairs on internodes.*—Absent.

*Anthocyanin coloration of buds.*—Absent or very weak.

Tendrils:

*Distribution on the shoot at full flowering.*—Continuous.

*Thickness.*—Thick.

*Color.*—Near Yellow-green 144B.

*Form.*—Bifurcated.

*Number of consecutive tendrils.*—Up to 2.

*Length of tendril.*—Medium, approximately 8 cm.

LEAVES

Young leaves:

*Color of upper surface of first* 4 *distal unfolded leaves.*—Near Yellow-green 144A.

*Average intensity of anthocyanin coloration of six distal leaves prior to flowering.*—Weak.

*Density of prostrate hairs between veins at lower surface of* 4*th distal unfolded leaf.*—Very sparse.

*Density of erect hairs between veins at lower surface of* 4*th distal unfolded leaf.*—Absent.

*Density of prostrate hairs on veins at lower surface of* 4*th distal unfolded leaf.*—Very sparse.

*Density of erect hairs on veins at lower surface of* 4*th distal unfolded leaf.*—Absent.

Mature leaves:

*Average length.*—Approximately 135 mm.

*Average width.*—Approximately 188 mm.

*Size of blade.*—Large.

*Shape of blade.*—Circular.

*Number of lobes.*—Approximately 5.

*Anthocyanin coloration of main veins on the upper side of the blade.*—Very weak.

*Mature leaf profile.*—Flat.

*Blistering surface of blade upper surface.*—Absent.

*Leaf blade tip.*—In the plane of the leaf.
*Undulation of margin.*—Slight.
*Thickness.*—Medium.
*Undulation of blade between main and lateral veins.*—Absent.
*Shape of teeth.*—Both sides convex.
*Length of teeth.*—Long.
*Ratio length/width of teeth.*—Small.
*General shape of petiole sinus.*—Slightly open.
*Tooth at petiole sinus.*—Absent.
*Petiole sinus limited by veins.*—Absent.
*Shape of upper lateral sinus.*—Lobes slightly overlapping.
*Depth of upper lateral sinus.*—Medium.
*Density of prostrate hairs between veins on lower surface of blade.*—Absent.
*Density of erect hairs between veins on lower surface of blade.*—Absent.
*Density of prostrate hairs on main veins on lower surface of blade.*—None or very sparse.
*Density of erect hairs on main veins on lower surface of blade.*—None or very sparse.
*Density of prostrate hairs on main veins on upper surface of blade.*—Absent.
*Autumn coloration of leaves.*—Near Greyed-yellow 162A, near Yellow-green 153D. Slow to develop. Normally frost kills leaves before extensive color change.

Upper surface:
*Color.*—Near Green 139A.
*Surface texture.*—Smooth.
*Surface appearance.*—Dull.

Lower surface:
*Color.*—Near Green 139B.
*Anthocyanin coloration of main veins on lower leaf surface.*—Absent.
*Glossiness.*—Weak.
*Pubescence.*—Absent.
*Surface texture.*—Smooth.
*Surface appearance.*—Dull.

Petiole:
*Length of petiole.*—Long, approximately 13.2 cm.
*Length of petiole compared to middle vein.*—Equal.
*Diameter.*—Approximately 3.1 mm.
*Density of prostrate hairs on petiole.*—None.
*Density of erect hairs on petiole.*—None.
*Shape of base of petiole sinus.*—V-shaped.
*Color.*—Near Yellow-green 145A.

Buds:
*Shape.*—Slightly pointed.
*Size.*—Medium, approximately 4 mm×5 mm.
*Position.*—Markedly held out, approximately 45° angle.
*Cane bud fruitfulness.*—Basal most fruitful.
*Time of bud burst.*—Early, Mar. 11, 2004.

FLOWERS

General:
*Flowers sex.*—Hermaphrodite.
*Length of first inflorescence.*—Long, approximately 31 cm.
*Position of first flowering node.*—Fourth to fifth.
*Number of inflorescences per shoot.*—Up to 1.
*Date of full bloom.*—Apr. 19, 2004.
*Time of bloom.*—Very early.
*Size (diameter of fully open flower).*—Medium, approximately 5 mm.

FRUIT

General:
*Ripening period.*—Medium, approximately 11 days ahead of Thompson Seedless variety.
*Use.*—Fresh market.
*Keeping quality.*—Good.
*Shipping quality.*—Good.
*Date of first harvest.*—Jul. 21, 2004.
*Solids-sugar.*—Medium (≈18%).
*Refractometer test.*—Approximately 17.0.
*Acid.*—High, approximately 4.7 gr./L tartaric acid.
*Juice pH.*—Approximately 3.41.
*Resistance.*—Neither resistance nor susceptibility to diseases or pests has been observed in this variety.

Cluster:
*Branch size (peduncle excluded).*—Small.
*Bunch length (peduncle excluded).*—Short, approximately 28 cm.
*Bunch width.*—Approximately 18.4 cm.
*Bunch weight.*—Low, approximately 748.4 g.
*Bunch density.*—Loose.
*Number of berries.*—Approximately 213.4.
*Form.*—Cylindrical.

Peduncle:
*Length of peduncle.*—Medium, approximately 54 mm.
*Lignification of peduncle.*—Very low.
*Color.*—Near Yellow-green 148A.

Berry:
*Size.*—Medium.
*Uniformity of size.*—Uniform.
*Berry weight.*—Medium, approximately 3.88 gr.
*Shape.*—Elliptic, ovate.
*Presence of seeds.*—Rudimentary.
*Cross section.*—Circular.
*Dimensions.*—Longitudinal axis: Approximately 20.66 mm. Horizontal axis: Approximately 17.38 mm.
*Skin color (without bloom).*—Near Greyed-purple 187A.
*Juiciness of flesh.*—Very juicy.
*Berry firmness.*—Very firm.
*Particular flavor.*—None.
*Bloom (cuticular wax).*—Very weak.
*Pedicel length.*—Intermediate, approximately 6.96 mm.
*Berry separation from pedicel.*—Easy.
*Visibility of hilum.*—Unclear.

Skin:
*Thickness.*—Medium.
*Texture.*—Tender.
*Reticulation.*—Absent.
*Roughness.*—Absent.
*Tenacity.*—Tenacious to flesh.

What is claimed is:

1. A new and distinct variety of grapevine as herein illustrated and described.

* * * * *